[12] United States Patent  
Jevanthi et al.

(10) Patent No.: US 7,033,608 B1
(45) Date of Patent: *Apr. 25, 2006

(54) "BURST-FREE" SUSTAINED RELEASE POLY-(LACTIDE/GLYCOLIDE) MICROSPHERES

(75) Inventors: Ramasubbu Jevanthi, Columbia, MD (US); John E. Van Hamont, Fort Meade, MD (US); Phil Friden, Bedford, MA (US); Robert H. Reid, Fairfield, PA (US); F. Donald Roberts, Dover, MA (US); Charles E. McQueen, Olney, MD (US); Jean A. Setterstrom, Silver Spring, MD (US)

(73) Assignee: The United States of America as represented by the Secretary of the Army, Washington, DC (US)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

This patent is subject to a terminal disclaimer.

(21) Appl. No.: 09/337,945

(22) Filed: Jun. 22, 1999

Related U.S. Application Data

(63) Continuation of application No. 08/590,973, filed on Jan. 24, 1996, now abandoned, which is a continuation-in-part of application No. 08/446,149, filed on May 22, 1995, now abandoned.

(51) Int. Cl.
*A61K 9/14* (2006.01)
*A61K 9/16* (2006.01)
*A61K 9/50* (2006.01)

(52) U.S. Cl. .................. 424/490; 424/489; 424/491; 424/493; 424/496; 424/501
(58) Field of Classification Search ............ 424/489, 424/490, 491, 493, 496, 501
See application file for complete search history.

(56) References Cited

U.S. PATENT DOCUMENTS

| 3,540,444 A | 11/1970 | Moreland ............... 128/173 |
| 3,773,919 A | 11/1973 | Boswell ................... 424/19 |
| 3,788,315 A | 1/1974 | Laurens ................ 128/173 H |

(Continued)

FOREIGN PATENT DOCUMENTS

EP 0052510 B2 10/1994

(Continued)

OTHER PUBLICATIONS

Gilding, Biodegradable polymers for use in surgery-polyglycolic/poly (ac c acid) homo- and copolymers: 1, Polymer, vol. 20, Dec. 1979, pp. 1459-1464.

(Continued)

*Primary Examiner*—Thurman K. Page
*Assistant Examiner*—S. Tran
(74) *Attorney, Agent, or Firm*—Elizabeth Arwine

(57) ABSTRACT

Novel burst-free, sustained release biocompatible and biodegrable microcapsules which can be programmed to release their active core for variable durations ranging from 1–100 days in an aqueous physiological environment. The microcapsules are comprised of a core of polypeptide or other biologically active agent encapsulated in a matrix of poly (lactide/glycolide) copolymer as a blend of uncapped (free carboxyl end group) and end-capped forms ranging in ratios from 100/0 to 1/99.

4 Claims, 8 Drawing Sheets

U.S. PATENT DOCUMENTS

| | | | |
|---|---|---|---|
| 4,166,800 A | 9/1979 | Fong | 252/316 |
| 4,384,975 A | 5/1983 | Fong | 427/213.36 |
| 4,530,840 A | 7/1985 | Tice et al. | 514/179 |
| 4,542,025 A | 9/1985 | Tice et al. | 424/78 |
| 4,585,482 A | 4/1986 | Tice et al. | 106/15.05 |
| 4,622,244 A | 11/1986 | Lapka et al. | 427/213.32 |
| 4,637,905 A | 1/1987 | Gardner | 264/4.3 |
| 4,675,189 A | 6/1987 | Kent et al. | 424/490 |
| 4,798,786 A | 1/1989 | Tice et al. | 435/177 |
| 4,835,139 A | 5/1989 | Tice et al. | 514/15 |
| 4,863,735 A | 9/1989 | Kohn et al. | 524/422 |
| 4,897,268 A | 1/1990 | Tice et al. | 424/422 |
| 4,938,763 A | 7/1990 | Dunn et al. | 604/891.1 |
| 4,941,880 A | 7/1990 | Burns | 604/143 |
| 5,000,886 A | 3/1991 | Lawter et al. | 264/4.3 |
| 5,019,096 A | 5/1991 | Fox, Jr. et al. | 623/1 |
| 5,059,187 A | 10/1991 | Sperry et al. | 604/290 |
| 5,064,413 A | 11/1991 | McKinnon et al. | 604/70 |
| 5,075,109 A | 12/1991 | Tice et al. | 424/88 |
| 5,102,872 A | 4/1992 | Singh et al. | 514/21 |
| 5,129,825 A | 7/1992 | Discko, Jr. | 433/90 |
| 5,133,701 A | 7/1992 | Han | 604/289 |
| 5,236,355 A | 8/1993 | Brizzolara et al. | 433/80 |
| 5,278,202 A | 1/1994 | Dunn et al. | 523/113 |
| 5,290,494 A | 3/1994 | Coombes et al. | 264/41 |
| 5,360,610 A | 11/1994 | Tice et al. | 424/426 |
| 5,384,133 A | 1/1995 | Boyes et al. | 424/501 |
| 5,407,609 A | 4/1995 | Tice et al. | 264/46 |
| 5,417,986 A | 5/1995 | Reid et al. | 424/499 |
| 5,429,822 A | 7/1995 | Gresser et al. | 424/426 |
| 5,500,228 A | 3/1996 | Lawter et al. | 424/486 |
| 5,538,739 A | 7/1996 | Bodmer et al. | 424/501 |
| 5,639,480 A | 6/1997 | Bodmer et al. | 424/501 |
| 5,643,605 A | 7/1997 | Cleland et al. | 424/489 |
| 5,648,096 A | 7/1997 | Gander et al. | 424/489 |
| 5,650,173 A | 7/1997 | Ramstack et al. | 424/489 |
| 5,688,530 A | 11/1997 | Bodmer et al. | 424/501 |
| 5,693,343 A | 12/1997 | Reid et al. | 424/491 |
| 5,762,965 A | 6/1998 | Burnett et al. | 424/499 |
| 5,811,128 A | 9/1998 | Tice et al. | 424/501 |
| 5,814,344 A | 9/1998 | Tice et al. | 424/501 |
| 5,820,883 A | 10/1998 | Tice et al. | 424/501 |
| 5,853,763 A | 12/1998 | Tice et al. | 424/489 |
| 6,372,245 B1 * | 4/2002 | Bowman et al. | 424/427 |
| 6,528,097 B1 * | 3/2003 | Vaughn et al. | 424/501 |
| 6,600,010 B1 * | 7/2003 | Mao et al. | 528/400 |
| 6,855,331 B1 * | 2/2005 | Vook et al. | 424/422 |

FOREIGN PATENT DOCUMENTS

WO      WO 9726869 A1 *    7/1997

OTHER PUBLICATIONS

Biotechnology News, Aug. 22, 1997, vol. 17, No. 20, Topical DNA vaccine elicits Immune response.

Hall, et al., Purification and Analysis of Colonization Factor Antigen I, Coli Surface Antigen 1, and Coli Surface ANtigen 3 Fimbriae from Enterotoxigenic Escherichia Coli, Journal of Bacteriology, Nov. 1989, p. 6372-6374, vol. 171, No. 11.

Evans, et al. Purification and Characterization of the CFR/I Antigen of Enterotoxigenic Escherichia coli, Infection and Immunity, Aug. 1979, p. 738-748, vol. 25.

Karjalainen, et al., Molecular Cloning and Nucleotide Sequence of the Colonization Factor Antigen I Gene of Escherichia coli, Infecction and Immunity, Apr. 1989, p. 1126-1130, vol. 57.

Jeyanthi, et al., Novel, Burst Free Programmable Biodegradable Microspheres For Controlled Release of Polypeptides, Proceedings Int. Symp. control Release Bioact. Mater. (1996) p. 351-352.

Yeh, A novel emulsification-solvent extraction technique for production of protein loaded biodegradable microparticles for vaccine and drug delivery, Journal of Controlled Release, 33 (1005) 437-445.

Yan, Characterization and morphological analysis of protein-loaded poly(lactide-co-glycolide) microparticles prepared by watewr-in-oil-in-water emulsion technique, Journal of Controlled Release, 32 (1994) 231-241.

Wang, et al., Influence of formulation methods on the in vitro controlled release of protein from poly (ester) Microspheres Journal of Controlled Release, 17 (1991) 23-32.

Brown, Wonder Drugs' Losing Healing Aura, The Washing Post, Jun. 26, 1995, A section.

Setterstrom, Controlled Release of Antibiotics From biodegradable Microcapsules For Wound Infection Control, Chemical Abstracts, 1983, pp. 215-226.

Perez-Casal, et al., Gene Encoding the Major Subunit of CS1 Pili of Human Enterotoxigenic Escherichia Coli, Infection and Immunity, Nov., 1990, p. 3594-3600, vol. 58, No. 11.

Jordi, et al., Analysis of the first two genes of the CSI fimbrial operon in human enteroxigenic Escherichia coli of serotype 0139: H28, FEMS Microbiology Letters 80, (1991) p. 265-270.

Tan, et al., Mapping the Antigenic Epitopes of Human Dihydrofolate Reductase by Systematic Synthesis of Peptides on solid Supports, The Journal of Biological Chemistry, vol. 265, No. 14, Issue of May 15, pp. 8022-8026 (1990).

McConnel, et al., Antigenic homology within human enterotoxigenic Esherichia coli fimbrial colonization factor antigens: CFA/I, coli-surface-associated antigens (CS)1, CS2, CS4 and CS17, FEMS Microbiology Letters 61 (1989) 105-108.

Van der Zee, Efficient mapping and characterization of a T cell epitope by the simultaneous synthesis of multiple peptides, Eur. J. Immunol. 1989, 19: 43-47.

Cassels, et al., Analysis of Escherichia coli Colonization Factor Antigen I Linear B-Cell Epitopes, as Determined by Primate Responses, following protein Sequence Verification, Infection and Immunity, Jun. 1992, p. 2174-2181, vol. 60, No. 6.

Romagnoli, et al. Peptide-MHC Interaction: A Rational Approach to Vaccine Design, Inter, RE. Immunol. 6, 1990, 00 61-73.

Maister, First Oral AIDS Vaccine Trials Near, BioWorld Today, Tuesday, Apr. 19, 1994, p. 4.

Rognan, et al., Molecular Modeling of an Antigenic Complex Between a Viral Peptide and a Class I Major Histocompatibility Glycoprotein, Proteins Structure, Function and Genetics 13 70-85 (1992).

Browm, A hypothetical model of the foreign antigen biinding site of Class II histocompatibility molecules, Nature, vol. 332, Apr. 28, 1988, p. 845-850.

* cited by examiner

"BURST-FREE" SUSTAINED RELEASE POLY-(LACTIDE/GLYCOLIDE) MICROSPHERES

CROSS REFERENCE

This application is a continuation application of U.S. patent application Ser. No. 08/590,973, filed Jan. 24, 1996 now abandoned, which is a continuation-in-part of U.S. patent application Ser. No. 08/446,149, filed May 22, 1995 now abandoned.

GOVERNMENT INTERESTS

The invention described herein may be manufactured, licensed and used by or for governmental purposes without the payment of any royalties to us thereon.

FIELD OF THE INVENTION

This invention relates to providing novel biocompatible and biodegradable microspheres for burst-free programmable sustained release of biologically active agents, inclusive of polypeptides, over a period of up to 100 days in an aqueous physiological environment.

BACKGROUND OF THE INVENTION

Several publications and patents are available for sustained release of active agents from biodegradable polymers, particularly, poly(lactide/glycolides) (PLGA). Prior usages of PLGA for controlled release of polypeptides have involved the use of molar ratios of lactide/glycolide (L/G) of 75/25 to 100/0 for molecular weights >20,000. Further prior art preparations of PLGA utilized fillers or additives in the inner aqueous layer to improve the stability and encapsulation efficiency and/or to increase the viscosity of the aqueous layer, thereby modulating polymer hydrolysis and the biologically active agent or polypeptide release.

In addition, the prior art use of PLGA copolymers were end-capped, in that the terminal carboxyl end groups were blocked. In these end-capped co-polymers, the microcapsule preparations exhibited a low to moderate burst release of ~10–40% of the entrapped polypeptide in the first 24 hours after placement in an aqueous physiological environment. In part, these characteristics are due to the use of fillers in the inner aqueous phase. Further, a 1-month release of polypeptide is known with the use of a 75/25 co-polymer of PLGA of Mw <20,000.

Investigations in controlled release research has been proceeding especially to obtain a 1 to 2 month delivery system for biologically active agents or polypeptides using poly(lactide/glycolide) polymers. However, most of these systems have one or more of the following problems: Poor encapsulation efficency and large 'burst release' followed by an intermediate 'no release' or 'lag phase' until the polymer degrades. In general, release from these polymers occur over a period from about 4 weeks to about several months. In addition, in order to achieve this release a 50/50 copolymer of MW >30,000 or a 75/25 copolymer of Mw >10,000 are employed which often results in residual polymer remaining at the site of administration long after the release of active core.

SUMMARY OF THE INVENTION

This invention provides biocompatible and biodegradable microspheres that have been designed for novel, burst free, programmable sustained release of biologically active agents, including polypeptides over a period of up to 100 days in an aqueous physiological environment.

Unlike currently available release systems, which rely on the use of fillers/additives such as gelatin, albumin, dextran, pectin, polyvinyl pyrrolidone, polyethylene glycol, sugars, etc., and are still prone to low encapsulation efficiencies and "burst effects", this invention achieves high encapsulation and "burst-free" release without the use of any additive. In this invention, burst-free, programmable sustained release is achieved through the use of a unique blend of the 'uncapped' and end-capped forms of poly(lactide/glycolide) polymer in the molecular weight range of 2,000 to 60,000 daltons.

In general, microspheres described in this invention are produced by a unique emulsification technique wherein an inner water-in-oil (w/o) emulsion is stabilized by dispersing in a solvent-saturated aqueous phase containing an emulsion stabilizer. A ternary w/o/w emulsion is then formed by emulsifying the above w/o emulsions in an external pre-cooled aqueous phase containing an o/w emulsifier. Essentially, the inner w/o emulsion is comprised of an aqueous layer containing from ~2 to about 20% (w/w) of the active agent to be entrapped and an oil layer containing poly (lactide/glycolide) copolymer in concentrations ranging from ~5 to about—50% (w/w oil phase). The copolymer includes molecular weight ranging from 2,000 to about 60,000 daltons, with molar composition of lactide/glycolide from 90/10 to 40/60 and a blend of its uncapped and end-capped forms in a ratio of 100/0 to 1/99. Very high encapsulation efficiencies of about 80 to 100% are achieved depending on polymer molecular weight and structural form.

Programmable release of active core over variable durations between 1–100 days is achieved by a judicious selection of process parameters such as polymer concentration, peptide concentration and the aqueous/oil phase ratio.

This invention is particularly suitable for high encapsulation efficiencies and burst-free, continuous programmable release of polypeptides of molecular weights ranging from 1,000 to about 250,000 daltons, and also other biologically active agents over a period of 1–100 days. A uniqueness of the invention is that when using a 100/0 blend of the uncapped and capped polymer, the final phase of active core release is concurrent with the complete solubilization of the polymer to innocuous components, such as lactic and glycolic acids. This is a significant advantage over the currently available 30 day—release systems wherein a major regulatory concern is about toxicity of residual polymer at the site of administration, long after release of the active core.

The microcapsules described in this invention are suitable for administration via several routes such as parenteral (intramuscular, subcutaneous), oral, topical, nasal, rectal and vaginal routes.

DETAILED DESCRIPTION OF THE INVENTION

Figure 1:
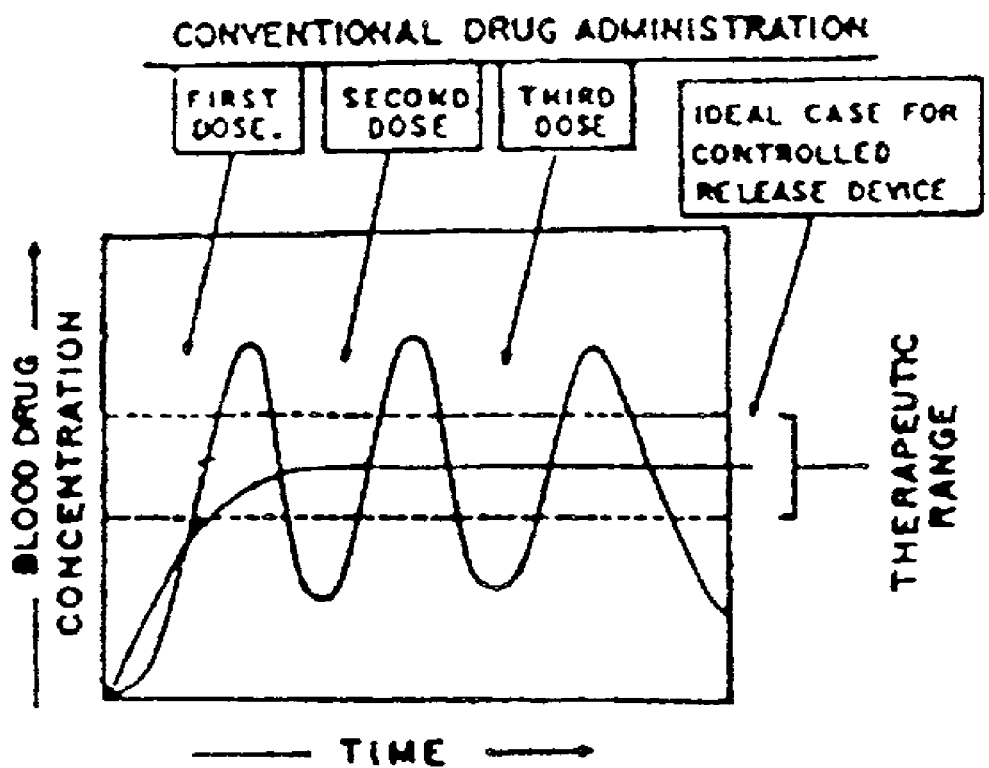
FIG. 1 shows a comparison of drug release from a conventional system versus a controlled release system. Peak and valley levels from conventional administrations are shown, in contrast to the steady therapeutic levels from the controlled release administration.

This invention relates to the design of biocompatible and biodegradable microspheres for novel, programmable sustained release of biologically active agents, including polypeptides over a period of up to 100 days in an aqueous physiological environment with little or no burst release.

Unlike currently available release systems which rely on the use of fillers/additives such as gelatin, albumin, dextran, pectin, polyvinyl pyrrolidone, polyethylene glycol, sugars, etc., and are still prone to low encapsulation efficiencies and "burst effects", this invention achieves high encapsulation efficiency and 'burst-free' release without the use of any additive. In this invention, burst-free, programmable sustained release is achieved through the use of a unique blend of the 'uncapped' and end-capped forms of poly (lactide/glycolide) polymer.

The 'uncapped' form refers to "poly(lactide/glycolide) with free carboxyl end groups" which renders the polymer more hydrophilic compared to the routinely used end-capped form. Currently used 'end-capped' polymer hydrates between 4–12 weeks depending on the molecular weight, resulting in an intermediate 'no release' or a 'lag phase'. The uncapped polymer hydrates typically between 5 to 60 days depending on the molecular weight, thus releasing its core continuously without a lag phase. A careful blend of the two forms and appropriate molecular weights and L/G ratios, results in a continuous release between 1 to 100 days. In addition, release within this time is programmable by a judicious selection of process parameters such as polymer concentration, peptide concentration and the aqueous/oil phase ratio.

The copolymer in this invention includes molecular weight ranging from 2,000 to 60,000 daltons, a lactide/glycolide ratio of 90/10 to 40/60 and a blend of the uncapped/capped forms in the ratio of 100/0 to 1/99. The molecular weight of the polypeptide may be in the range of 1000 to 250,000 daltons while that of other biologically active agents may range from 100 to 100,000 daltons.

Microcapsules described in this invention are prepared by a unique aqueous emulsification techinique which has been developed for use with the uncapped polymer to provide superior sphere morphology, sphere integrity and narrow size distribution. This is accomplished by first preparing an inner water-in-oil (w/o) by mixing the solutions of polymer in an organic solvent such as methylene chloride and the biologically active agent in water. This is followed by stabilization of the w/o emulsion in a solvent-saturated aqueous solution containing an o/w emulsifier such as polyvinyl alcohol. A ternary emulsion is then formed by emulsifying the w/o emulsion in an external aqueous phase containing the same emulsifier as above at concentrations ranging from 0.25–1% w/v. Microcapsules are hardened upon solvent removal by evaporation, rinsed to remove residual emulsifier and lyophilized. Low temperature is used both at the time of primary emulsification (w/o emulsion formation) and during the formation of the final w/o/w emulsion to achieve stable emulsion and superior sphere characteristics.

In the context of the invention, a biologically active agent is any water-soluble hormone drugs, antibiotics, antitumor agents, antiinflammatory agents, antipyretics, analgesics, antitussives, expectorants, sedatives, muscle relaxants, antiepileptics, antiulcer agents, antidepressants, antiallergic drugs, cardiotonics, antiarrhythmic drugs, vasodilators, antihypertensives, diuretics, anticoagulants, antinarcotics, etc.

More precisely, applicants have discovered a pharmaceutical composition and process with the following itemized features:

1. A controlled release microcapsule pharmaceutical formulation for burst-free, sustained, programmable release of a biologically active agent over a duration from 1–100 days, comprising an active agent and a blend of uncapped and end-capped biodegradable poly (lactide/glycolide).
2. The pharmaceutical formulation of item 1, wherein the biodegradable poly(lactide/glycolide) is a blend of uncapped and capped forms, in ratios ranging from 100/0 to 1/99.
3. The microcapsules of items 1 or 2 wherein the copolymer (lactide to glycolide L/G) ratio for uncapped and end-capped polymer is 52/48 to 48/52.
4. The microcapsules of items 1 or 2 wherein the copolymer L/G ratio for uncapped and end-capped polymer is 90/10 to 40/60.
5. The microcapsules of items 1 or 2 or 3 or 4 wherein the molecular weight of the copolymer is between 2,000–60,000 daltons.
6. The microcapsules of items 1 or 2 or 3 or 4 or 5 wherein the biologically active agent is a peptide or polypeptide.
7. The microcapsules of item 6, wherein said polypeptide is histatin consisting of 12 amino acids and having a molecular weight of 1563.
8. The microcapsules of items 1 or 2 or 3 or 4 or 5 or 6 characterized by the capacity to completely release histatin in an aqueous physiological environment from 1–35 days with a 100/0 blend of uncapped and end-capped poly(lactide/glycolide) having a L/G ratio of 48/52 to 52/48, and a molecular weight <15,000.

9. The microcapsules of items 1 or 2 or 3 or 4 or 5 or 6 characterized by the capacity to completely release histatin in an aqueous physiological environment from 18–40 days with a 100/0 blend of uncapped and end-capped poly(lactide/glycolide) having a L/G ratio of 48/52 to 52/48 and a molecular weight range of 28,000–40,000.

10. The microcapsules of items 1 or 2 or 3 or 4 or 5 or 6 characterized by the capacity to release up to 90% of the histatin in an aqueous physiological environment from 28–70 days with a 0/100 blend of uncapped and end-capped poly(lactide/glycolide) having a L/G ratio of 48/52 to 52/48 and a molecular weight range of 10,000–40,000 daltons.

11. The microcapsules of items 1 or 2 or 3 or 4 or 5 or 6 characterized by the capacity to release up to 80% of histatin in an aqueous physiological environment from 56–100 days with a 0/100 blend of uncapped and end-capped poly(lactide/glycolide) having a L/G ratio of 75/25 and a molecular weight of <15,000 daltons.

12. The microcapsules of items 7 or 8 or 9 or 10 or 11 having analogs of histatin with chain lengths of from 11–24 amino acids of molecular weights from 1,500–3,000 daltons and characterized by the following structures:
   1. D S H A K R H H G Y K R K F H E K H H S H R G Y
   2. K R H H G Y K R K F H E K H H S H R G Y R
   3. K R H H G Y K R K F H E K H H S H R
   4. R K F H E K H H S H R G Y R
   5. A K R H H G Y K R K F H
   6. *A K R H H G Y K R K F H
   7. K R H H G Y K R K F
   * D-amino acid 13. The microcapsules of items 1 or 2 or 3 or 4 or 5 wherein the biologically active agent is a polypeptide Leutinizing hormone releasing hormone (LHRH) that is a decapeptide of molecular weight 1182 in its acetate form, and having the structure:
   p-E H W S Y G L R P G 14. The microcapsule of items 6 or 7 or 8 or 9 or 10 or 11 or 12 or 13 wherein the biologically active agent is a polypeptide having a molecular weight of from 1,000 to 250,000 daltons.

15. The microcapsules of items 6 or 7 or 8 or 9 or 10 or 11 or 12 or 13 or 14 wherein release profiles of variable rates and durations are achieved by blending uncapped and capped microspheres as a cocktail in variable amounts.

16. The microcapsules of items 6 or 7 or 8 or 9 or 10 or 11 or 12 or 13 or 14 wherein release profiles of variable rates and duration are achieved by blending uncapped and capped polymer in different ratios within the same microspheres.

17. The microcapsules of items 6 or 7 or 8 or 9 or 10 or 11 or 12 or 13 or 14 or 15 or 16 wherein the entrapped polypeptide is any of the vaccine agents against enterotoxigenic *E. coli* (ETEC) such as CFA/I,CFA/II,CS1, CS3,CS6 and CS17 and other ETEC-related enterotoxins.

18. The microcapsules of items 6 or 7 or 8 or 9 or 10 or 11 or 12 or 13 or 14 or 15 or 16 or 17 wherein the entrapped polypeptide consists of peptide antigens of molecular weight range of about 800–5000 daltons for immunization against enterotoxigenic *E. coli* (ETEC).

19. The microcapsules of items 1 or 2 or 3 or 4 or 5 wherein said biologically active agents are selected from the group consisting of water-soluble hormone drugs, antibiotics, antitumor agents, anti inflammatory agents, antipyretics, analgesics, antitussives, expectorants, sedatives, muscle relaxants, antiepileptics, anti-ulcer agents, antidepressants, antiallergic drugs, cardiotonics, antiarrhythmic drugs, vasodilators, antihypertensives, diuretics, anticoagulants, and antinarcotics, in the molecular weight range of 100–100,000 daltons.

20. The microcapsules of items 1 or 2 or 3 or 4 or 5 or 6 or 7 or 8 wherein said biodegradable poly(lactide/glycolide) is in an oil phase, and is present in about 1–50% (w/w).

21. The microcapsules of items 1 or 2 or 3 or 4 or 5 or 6 or 8 or 9 or 10 or 11 or 12 or 13 or 14 or 15 or 16 or 17 wherein concentration of the active agent is in the range of 0.1 to about 60% (w/w).

22. The microcapsules of items 1 or 2 or 3 or 4 or 5 or 6 or 8 or 9 or 10 or 11 or 12 or 13 or 14 or 15 or 16 or 17 wherein a ratio of the inner aqueous to oil phases is about 1/4 to 1/40(v/v).

23. A process for preparing controlled release microcapsule formulations characterized by burst-free, sustained, programmable release of biologically active agents comprising: Dissolving biodegradable poly (lactide/glycolide), in uncapped form in methylene chloride, and dissolving a biologically active agent or active core in water; adding the aqueous layer to the polymer solution and emulsifying to provide an inner water-in-oil (w/o) emulsion; stabilizing the w/o emulsion in a solvent-saturated aqueous phase containing a oil-in-water (o/w) emulsifier; adding said w/o emulsion to an external aqueous layer containing oil-in-water emulsifier to form a ternary emulsion; and stirring the resulting water-in-oil-in-water (w/o/w) emulsion for sufficient time to remove said solvent, and rinsing hardened microcapsules with water and lyophilizing said hardened microcapsules.

24. A process for preparing controlled release microcapsule formulations characterized by burst-free, sustained, programmable release of biologically active agents comprising:
   dissolving biodegradable poly(lactide/glycolide) in end-capped form in methylene chloride, and dissolving a biologically active agent or active core in water; adding the aqueous layer to the polymer solution and emulsifying to provide an inner water-in-oil emulsion; stabilizing the w/o emulsion in a solvent-saturated aqueous phase containing a oil-in-water (o/w) emulsifier; adding said w/o emulsion to an external aqueous layer containing oil-in-water emulsifier to form a ternary emulsion; and stirring a resulting water-in-oil-water (w/o/w) emulsion for sufficient time to remove said solvent; and rinsing hardened microcapsules with water; and lyophilizing said hardened microcapsules.

25. The process of items 23 or 24 wherein a solvent-saturated external aqueous phase is added to emulsify the inner w/o emulsion prior to addition of the external aqueous layer, to provide microcapsules of narrow size distribution range between 0.05–500 μm.

26. The process of items 23 or 24, wherein a low temperature of about 0–4° C. is provided during preparation of the inner w/o emulsion, and a low temperature of about 4–20° C. is provided during preparation of the w/o/w emulsion to provide a stable emulsion and high encapsulation efficiency.

27. The process of items wherein a 100/0 blend of uncapped and end-capped polymer is used to provide release of the active core in a continous and sustained manner without a lag phase.

28. The microcapsules of items 6, wherein, when the entrapped polypeptide is active at a low pH, such as LHRH, adrenocorticotropic hormone, epidermal growth factor, calcitonin released polypeptide is bioactive.

29. The microcapsules of items 6 or 7 or 8 or 9 or 10 or 11, wherein, when entrapped peptide such as histatin is inactive at a low pH, a pH-stabilizing agent of inorganic salts are added to the inner aqueous phase to maintain biological activity of the released peptide.

30. The microcapsules of items 6 or 7 or 8 or 9 or 10 or 11 wherein, when entrapped polypeptide such as histatin is inactive at a low pH, a non-ionic surfactant such as polyoxyethylene sorbitan fatty acid esters (Tween 80, Tween 60 and Tween 20) and polyoxyethylene—polyoxypropylene block copolymers (Pluronics) is added to the inner aqueous phase to maintain biological activity of the released polypeptide.

31. The microcapsules of items 29, wherein placebo spheres loaded with the pH-stabilizing agents are coadministered with polypeptide-loaded spheres to maintain the solution pH around the microcapsules and preserve the biological activity of the released peptide in instances where the addition of pH-stabilizing agents in the inner aqueous phase is undesirable for the successful encapsulation of the acid pH sensitive polypeptide.

32. The microcapsules of item 30 wherein placebo spheres loaded with non-ionic surfactant are coadministered with polypeptide-loaded spheres to maintain biological activity of the released peptide where the addition of non-ionic surfactants in the inner aqueous phase is undesirable for successful encapsulation of the acid pH sensitive polypeptide.

33. The microcapsules of items 1 or 2 or 3 or 4 or 5 or 6 or 8 or 9 or 10 or 11 or 12 or 13 or 14 or 15 or 16 or 17 comprising a blend of uncapped and capped polymer, wherein complete solubilization of the copolymer leaves no residual polymer at the site of administration and occurs concurrently with the complete release of the entrapped agent.

34. A process of using microcapsules of items 1 or 2 or 3 or 4 or 5 or 6 or 7 or 8 or 9 or 10 or 11 or 12 or 13 or 14 or 15 or 16 or 17 or 18 or 19 or 20 for human administration via parenteral routes, such as intramuscular and subcutaneous.

35. A process of using microcapsules of items 1 or 2 or 3 or 4 or 5 or 6 or 7 or 8 or 9 or 10 or 11 or 12 or 13 or 14 or 15 or 16 or 17 or 18 or 19 or 20 for human administration via topical route.

36. A process of using microcapsules of items 1 or 2 or 3 or 4 or 5 or 6 or 7 or 8 or 9 or 10 or 11 or 12 or 13 or 14 or 15 or 16 or 17 or 18 or 19 or 20 for human administration via oral routes.

37. A process of using microcapsules of items 1 or 2 or 3 or 4 or 5 or 6 or 7 or 8 or 9 or 10 or 11 or 12 or 13 or 14 or 15 or 16 or 17 or 18 or 19 or 20 for human admininstration via nasal, transdermal, rectal, and vaginal routes.

Conservation of Bioactivity of Polypeptides

As the polymer degrades rapidly, there is a precipitous drop in pH accompanied by the release of soluble oligomers in the microenvironment which may affect the biological activity of acid pH-sensitive peptides/proteins. In such instances, biological activity can be maintained by the use of inorganic salts or buffering agents in the inner aqueous phase codissolved with the peptide.

The following unique advantages are characteristics of this invention:

1. Burst-free, prolonged, sustained release of polypeptides and other biologically active agents from biocompatible and biodegradable microcapsules up to 100 days in an aqueous physiological environment without the use of additives in the core.
2. Release of active core programmable for variable durations over 1–100 days, by using a blend of uncapped and capped polymer of different molecular weights and copolymer ratio, and by manipulating the process parameters.
3. Complete release of the active core is concurrent with complete solubilization of the carrier polymer to innocuous components, such as lactic and glycolic acids, especially when using a 100/0 blend of uncapped/capped polymer. This is of tremendous significance, as most biodegradable polymers currently used for 1–30 day delivery, do not degrade completely at the end of the intended release duration, thereby causing serious concern of regulatory authorities on the effects of residual polymer at the site of administration.
4. Ease of administration of the microcapsules in various dosage forms via several routes, such as parenteral (intramuscular and sucutaneous), oral, topical, nasal, vaginal, etc.

The hydrophilic homo-and co-polymers based on D,L-lactide and glycolide contains hydrophilic adjusted homo- and co-polymers with free carboxylic end groups, and is characterized by the formula:

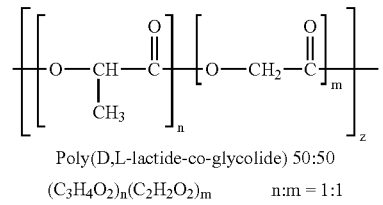

Poly(D,L-lactide-co-glycolide) 50:50

$(C_3H_4O_2)_n(C_2H_2O_2)_m$     n:m = 1:1

Wherein Z=Molecular Weight/130; for example Z=92 for Mw 12,000 and 262 for Mw 34,000.

While the molar ratio of the lactide to glycolide may vary, it is most preferred that the lactide to glycolide copolymer ratio be 50:50.

Reference is now made to FIG. 1 which depicts a blood-drug concentration versus time graph that shows conventional drug administration using a series of dosages compared to an ideal controlled release system. Unfortunately, many drugs have a therapeutic range, above which they are toxic and below which they are ineffective. Oscillating drug levels that are commonly observed following systemic administration causes alternating periods of ineffectiveness and toxicity. A sustained-release encapsulated biologically active agent or polypeptide preparation, ideally, will maintain the drug in the desired therapeutic range by means of a single dose, as depicted in the THERAPEUTIC RANGE in FIG. 1, where the ideal case for controlled release is shown.

Figure 2:
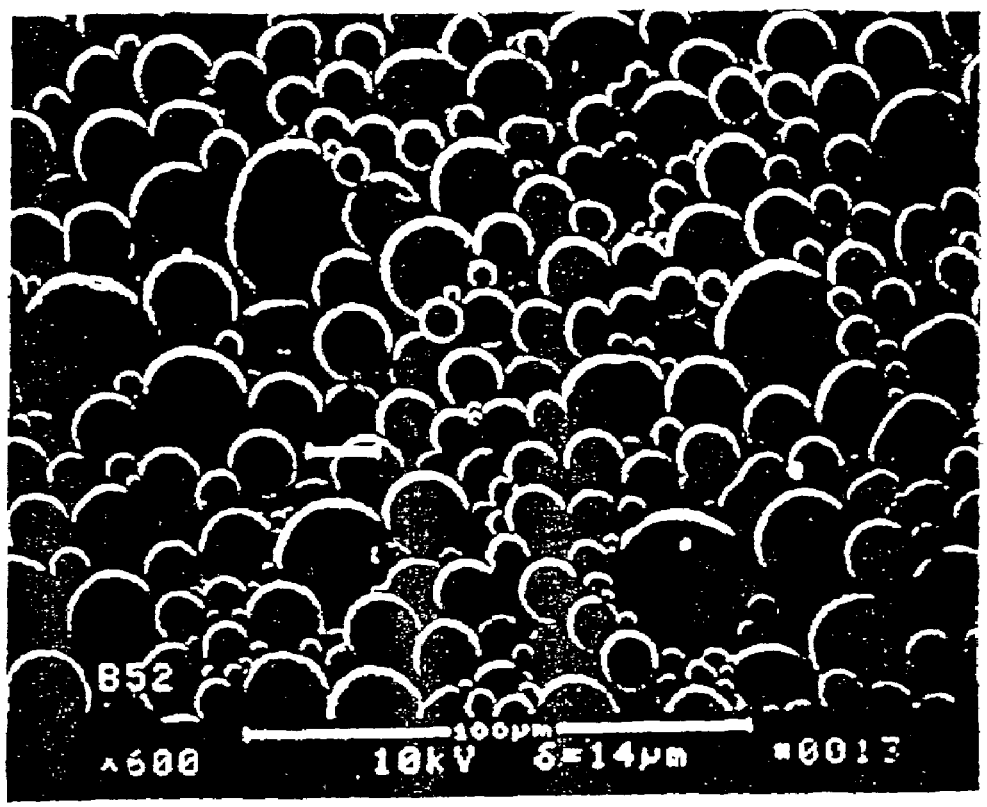
FIG. 2 shows a scanning electron micrograph of PLGA microspheres prepared by the process described in the invention using 50/50 uncapped polymer of Mw 8–12k dalton and shows superior sphere morphology, sphere integrity, and narrow size distribution.
Figure 2A:
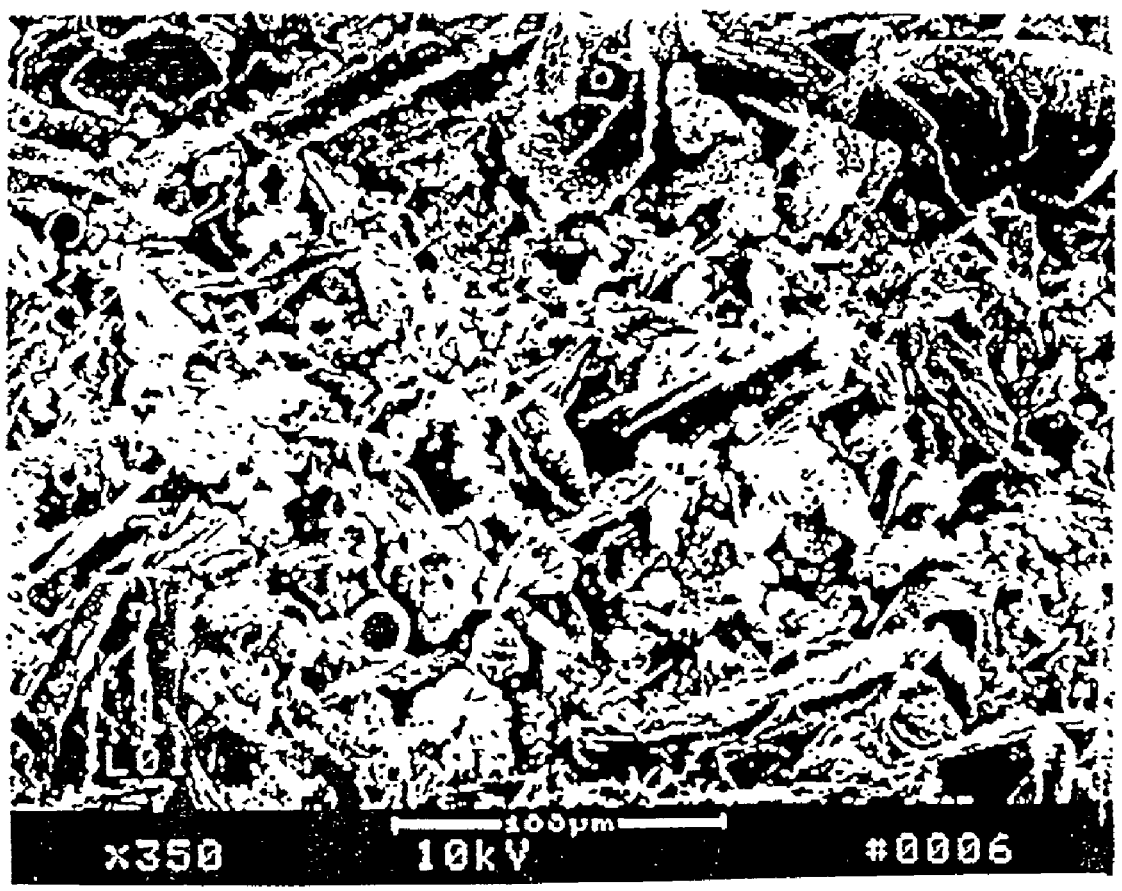
FIG. 2a shows a scanning electron micrograph of PLGA microspheres prepared by conventional solvent evaporation method using a 50/50 12k uncapped polymer of Mw 8-dalton.

In FIG. 2, there is shown a scanning electron micrograph of PLGA microspheres prepared using 50/50 uncapped polymer of Mw 8–12k dalton. The uncapped polymer has solid, smooth spherical surfaces, and is suited to provide a "burst free" release system.

Table I is a summarization of the microsphere process description for preparing a peptide system (Histatin peptide) having a controlled release over the course of from 1 to 100 days.

Release profiles can be modified by a judicious blend of uncapped and capped polymers either in separate microspheres or in the same microspheres. Release from microcapsule formulations 1 through 21 listed in Table 1, occur independently of each other and hence the cumulative release from blends of these formulations are additive. By blending several formulations of uncapped and end-capped microspheres, release curves of any desired duration can be tailored. In addition, based on the release characteristics of uncapped and end-capped polymers, blending of the two forms in a single formulation comprising different ratios of uncapped to capped polymer, would significantly influence the polymer hydration and hence release of the active core thereby providing release curves of any desirable pattern. Manipulation of polymer hydration and degradation resulting in modulation of release of active core is achieved by the addition of uncapped polymer to end-capped polymer in amounts as low as 1% up to 100%.

TABLE 1

Microcapsule compositions containing Histatin polypeptide

| Composition # | Polymer Description L/G Ratio & Type | Mol. Wt. (Mw × $10^3$) | Conc. in DCM (w/w) | Theoretical peptide Core Load (%) | Internal Phase Ratio (w/o) | Emulsification Technique |
|---|---|---|---|---|---|---|
| 1. | 50/50, U | 12 | 38 | 5 | 1:20 | A |
| 2. | 50/50, U | 12 | 18.5 | 2 | 1:20 | A |
| 3. | 50/50 | 34 | 10 | 5 | 1:20 | A |
| 4. | 50/50, U | 12 | 38 | 5 | 1:4 | A |
| 5. | 50/50 | 34 | 7 | 5 | 1:10 | B |
| 6. | 50/50 | 34 | 10 | 5 | 1:10 | B |
| 7. | 50/50 | 34 | 10 | 5 | 1:10 | A |
| 8. | 75/25 | 12 | 10 | 5 | 1:10 | B |
| 9. | 75/25 | 12 | 23.5 | 5 | 1:10 | B |
| 10. | 50/50 | 12 | 10 | 5 | 1:10 | B |
| 11. | 50/50 | 12 | 7 | 5 | 1:10 | B |
| 12. | 50/50, U | 12 | 10 | 5 | 1:10 | B |
| 13. | 50/50, U | 12 | 7 | 2.3 | 1:10 | B |
| 14. | 50/50, U | 12 | 10 | 5 | 1:10 | B |
| 15. | 50/50, U | 34 | 10 | 5 | 1:10 | B |
| 16. | 50/50, U | 12 | 10 | 5 | 1:10 | B |
| 17. | 50/50, U | 12 | 20 | 5 | 1:10 | B |
| 18. | 50/50, U | 12 | 40 | 5 | 1:10 | B |
| 19. | 50/50, U | 34 | 5 | 5 | 1:10 | B |
| 20. | 50/50, U | 34 | 10 | 5 | 1:10 | B |
| 21. | 50/50 U | 34 | 15 | 5 | 1:10 | B |

Acronyms:
L/G ratio: Copolymer composition of lactide/glycolide
DCM: Methylene Chloride
Mw: Molecular weight in daltons
A: w/o/w emulsification without an intermediate step for emulsion stabilization
B: w/o/w emulsification with an intermediate step for emulsion stabilization
U: Uncapped polymer While referring to Table 1 in conjunction with FIG. 3, it can be seen that the cumulative Histatin release from PLGA microspheres from several batches prepared using 50/50 and 75/25 uncapped and end-capped, polymer modulates release between 1 to 100 days by varying the process parameters. 1–35 days by uncapped 50/50, 18–56 days by capped 50/50 and 56–100 days by capped 75/25.

Figure 4:
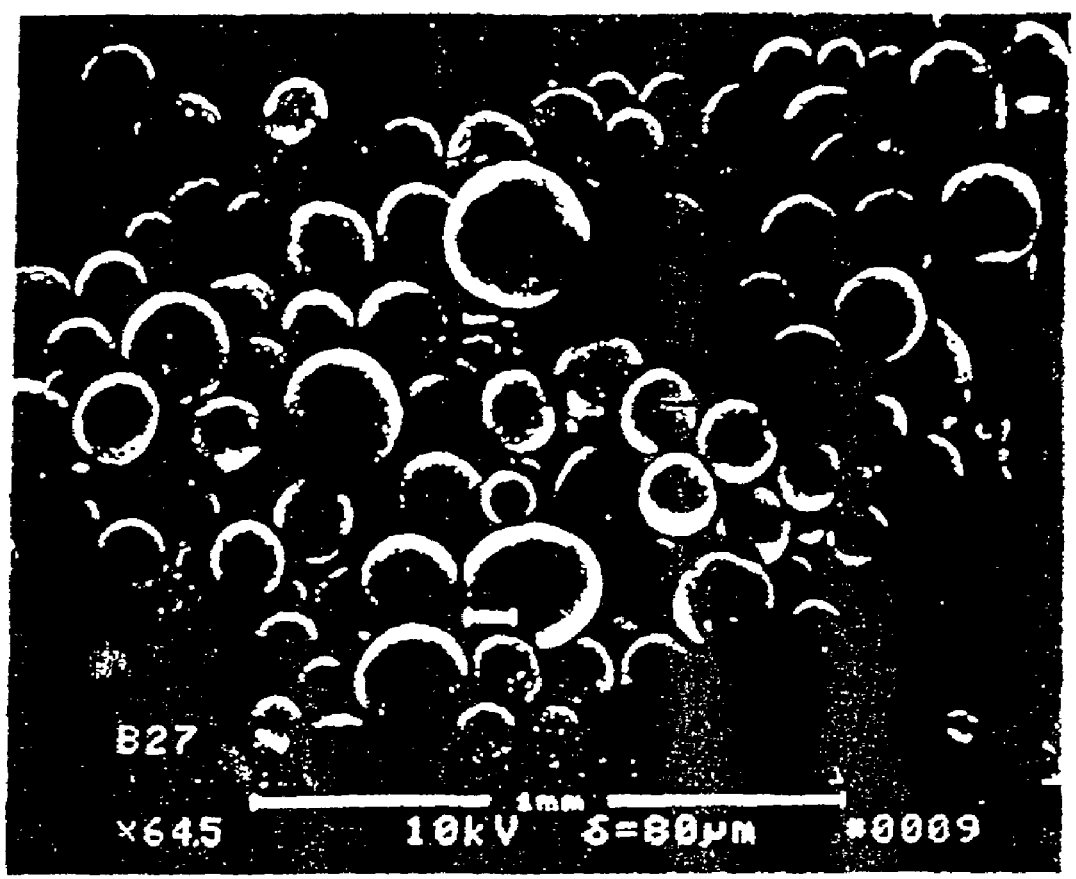
FIG. 4 shows a scanning electron micrograph of solid, smooth spherical surfaces of PLGA microspheres prepared by the method of in the invention using 50/50, end-capped polymer (of Mw 30–40k dalton).

In referring to FIG. 4, a view is provided through a scanning electron micrograph of PLGA microspheres designed for a one to two month release system prepared using end-capped polymer of Mw 30–40k daltons.

Figure 5:
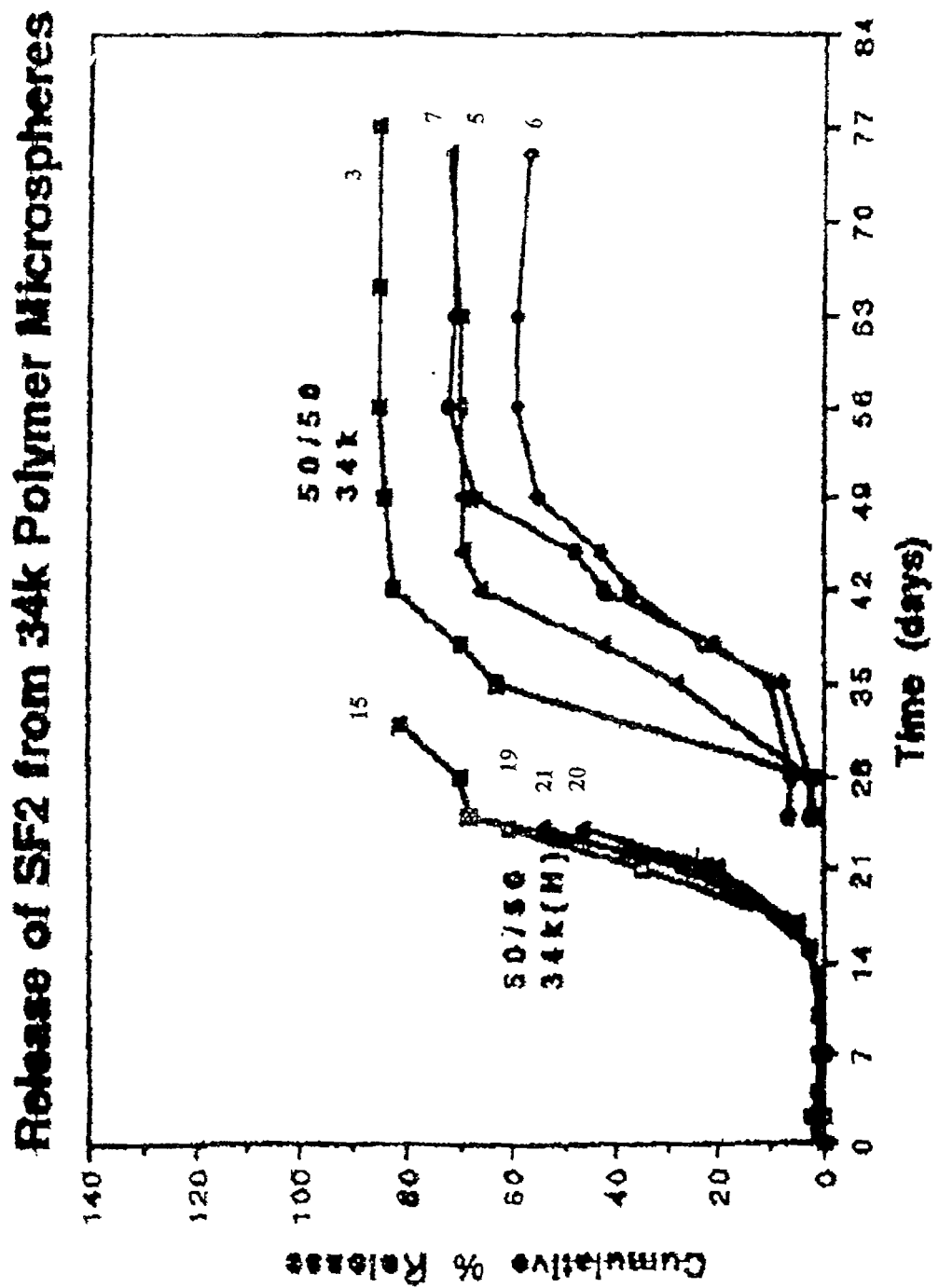
FIG. 5 shows cumulative Histatin release from PLGA microspheres, wherein the release profiles are from several batches prepared using 50/50, uncapped and end-capped polymer of Mw 30–40k daltons, and wherein the process parameters are varied to modulate release between 28 to 60 days.

FIG. 5 depicts the cumulative Histatin release from PLGA microspheres, in which the release profiles are from several batches prepared using 50/50, uncapped and capped polymer, and varying the process parameters to modulate release between 28 to 60 days.

Figure 6:
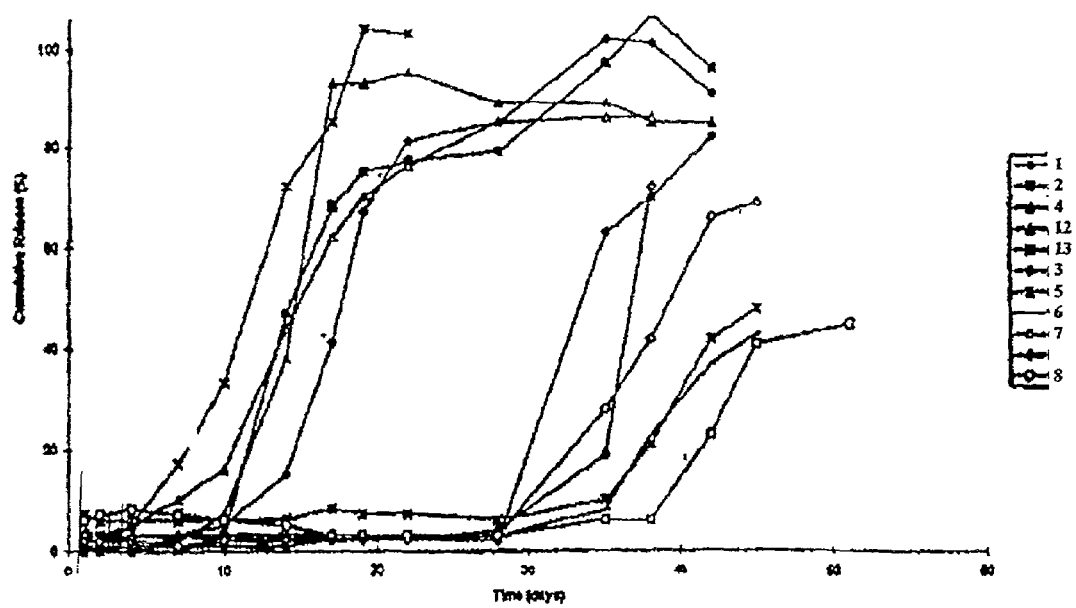
FIG. 6 shows cumulative Histatin release from PLGA microspheres, wherein combined release profiles from several batches have been prepared using 50/50, uncapped and end-capped polymer of Mw 8–40k daltons, while varying the process parameters to modulate release between 1 and 60 days.

FIG. 6 represents cumulative Histatin release from PLGA microspheres—these combined release profiles are from several batches prepared using 50/50 uncapped and capped polymer, and varying the process parameters to modulate release between 1–60 days.

In the context of the invention, a biologically active agent is any water-soluble antibiotics, antitumor agents, antipyretics analgesics, anti-inflammatory agents, antitussives, expectorants, sedatives, muscle relaxants, anti epileptics, antiulcer agents, anti-depressants, anti-allergic drugs, cardiotonics, antiarrhythmics drugs, vasodilators, antihypertensives, diuretics, anticoagulants, hormone drugs, anti-narcotics, etc.

In general, "burst free" sustained release delivery of biologically active agents from PLGA microspheres is accomplished in the context of this invention using of 90/10 to 40/60 molar ratios, and ratios of uncapped polymer to end-capped polymer of 100/0 to 1/99.

Figure 3:
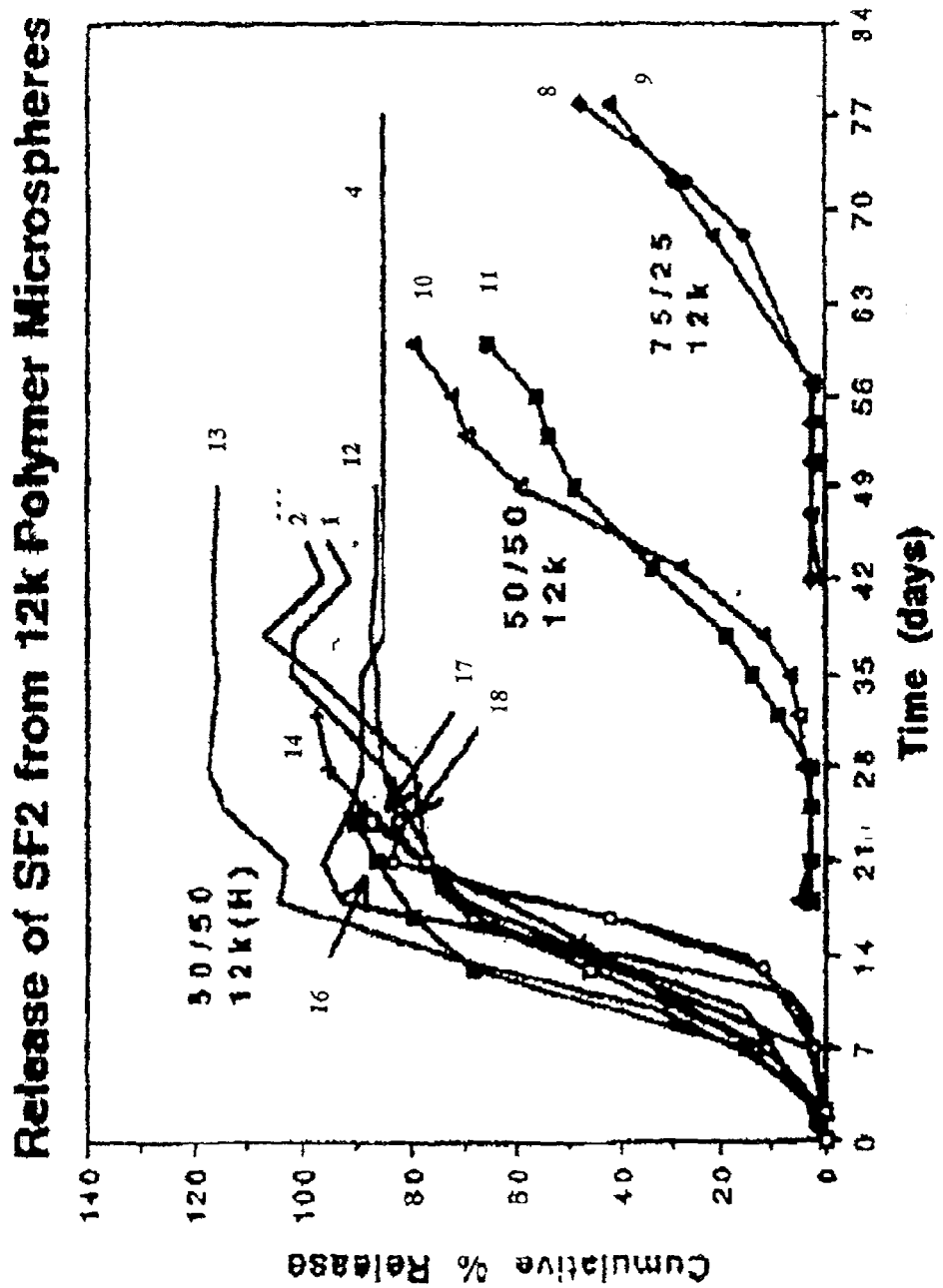
FIG. 3 shows cumulative Histatin release from PLGA microspheres, wherein release profiles from several batches are prepared using 50/50, uncapped polymer (of Mw 8–12k dalton) and wherein the process parameters are varied to modulate release between 1 and 35 days.

In general, the approaches for designing the biologically active agents encapsulated in the uncapped and combination uncapped/end-capped PLGA microspheres and characteristics of these encapsulants are briefly set forth below as follows:
  1. Providing PLGA microspheres of surface morphologies using 50/50 uncapped and capped polymers of Mw ~8–40K daltons as shown in FIGS. 2 and 4.
  2. Providing in vitro release of a polypeptide, Histatin from PLGA microspheres, as shown in FIGS. 3 and 5, using uncapped and capped polymer of Mw ~8–40K daltons and molar ratios such as 50/50 and 75/25.

For example, design of a 1–12 week bioactive compound release system is achieved using PLGA with the following specifications:
1. Polymer molecular weight:
    about 2–60K daltons
2. Copolymer molar ratio (L/G):
    90/10 to 40/60
3. Polymer end groups:
    uncapped and/or end-capped
and combining judiciously within the following parameters:
4. Polymer concentration
    from 5 to 50%
5. Inner aqueous to oil phase ratio:
    1:5 to 1:20 (v/v)
6. Peptide loads:
    from 2 to about 40% (w/w polymer)
and by using the unique aqueous emulsification method described in the invention.

The uniqueness and novelty of invention may generally be summarized in a brief way as follows:
1. Use of uncapped poly(lactide/glycolide) to achieve burst-free, continuous, sustained, programmable release of biologically active agents over 1–100 days.
2. Use of a unique aqueous emulsification system to achieve superior microsphere characteristics such as uniform sphere morphology and narrow size distribution.
3. Burst-free, prolonged, sustained release of polypeptides and other biologically active agents from biocompatible and biodegradable microcapsules up to 100 days in an aqueous physiological environment without the use of additives in the inner core.
4. Release of active core programmable for variable durations over 1–100 days by using a blend of uncapped and capped polymer for different molecular weights and copolymer ratios and manipulating the process parameters.
5. Complete release of the active core concurrent with complete solubilization of carrier polymer to innocuous components such as lactic and glycolic acids, especially when using a 100/0 blend of uncapped/capped polymer. This is of tremendous significance as most biodegradable polymers currently in use for 1–30 day delivery, do not degrade completely at the end of the intended release duration causing serious concern for regulatory authorities on the effects of residual polymer at the site of administration.
6. Ease of administration of the microcapsules in various dosages forms via several routes such as parenteral (intramusclar and subcutaneous), oral, topical, nasal, vaginal, etc.

The following examples are illustrative of, but not limitations upon the microcapsule compositions pertaining to this invention.

EXAMPLE 1

Polylactide/glycolide (PLGA) microcapsules are prepared by a unique aqueous emulsification technique which has been developed for use with the uncapped polymer to provide superior sphere morphology, sphere integrity and narrow size distribution (See FIGS. 2 and 4). This is accomplished by dissolving the polymer in a chlorinated hydrocarbon solvent such as methylene chloride and dissolving the biologically active agent in water. A w/o emulsion is then formed by mixing the solutions of polymer and the active agent by sonication, followed by emulsion stabilization in a solvent—saturated aqueous solution containing polyvinyl alcohol. A ternary emulsion is then formed by emulsifying the w/o emulsion in an external, pre-cooled aqueous phase containing polyvinyl alcohol (0.25–1% w/v). Microcapsules are hardened upon removal of solvent by evaporation, rinsed to remove any residual emulsifier, and then lyophilized.

Table 1 lists the microcapsule compositions, Nos. 1–21 thus prepared, consisting of a biologically active polypeptide, Histatin (composed of 12 amino acids and a molecular weight of 1563) and blends of uncapped and capped polymer of ratios 100/0 to 1/99, and having a lactide/glycolide ratio of 90/10 to 40/60, and a molecular weight range between 2000 to 60,000 daltons.

EXAMPLE 2

Microcapsule compositions are prepared as described in Example 1 wherein the copolymer L/G ratio is 48/52 to 52/48, and the ratio of uncapped/capped polymer is 100/0. The active core is Histatin (Mw 1563), the polymer molecular weight is <15,000 and the polymer concentrations vary from 7% to ~40% w/w. Compositions 1,2,4 12–14 and 16–18 are listed in Table 1.

Release profiles of the active core from the compositions in an aqueous physiological environment, such as phosphate-buffered saline, pH 7.0 maintained at 37±1° C. are plotted as cumulative percentage release versus time, and presented in FIG. 5.

Burst-free, variable release from 1–35 days is achieved by varying the polymer concentration from 7 to ~40% w/w in the oil phase.

EXAMPLE 3

Microcapsule compositions are prepared as described in Example 2, wherein the aqueous/oil ratio is varied from 1/4 to 1/20 (v/v). Compositions 1,2,4 and 12 are listed in Table 1.

Release profiles of the active core from the compositions in an aqueous physiological environment described in Example 2 are plotted as cumulative percentage release versus time, and presented in FIG. 5.

Burst-free, continuous release from 1–35 days, with different onset and completion times are achieved by selecting different w/o ratios in the inner core.

EXAMPLE 4

Microcapsule compositions are prepared as described in Example 2, wherein the polymer molecular weight is 28,000–40,000 and polymer concentrations vary from 5% to ~15% w/w. Compositions 19–21 are listed in Table 1.

Release profiles of the active core from the compositions in an aqueous physiological environment are described in Example 2 are plotted as cumulative percentage release versus time and presented in FIG. 5.

Burst-free, variable release from 18–40 days is achieved by varying the polymer concentration.

EXAMPLE 5

Microcapsule compositions are prepared as described in Example 2, wherein the ratio of uncapped/capped polymer is 1/99 and polymer concentrations vary between 5% to ~12% w/w. Compositions 10 and 11 are listed in Table 1.

Release profiles of the active core from the compositions in an aqueous physiological environment are described in Example 2, and plotted as cumulative percentage release versus time and presented in FIG. 3.

Burst-free, variable release from 28–70 days is achieved by varying the polymer concentration in the oil phase.

EXAMPLE 6

Microcapsule compositions are prepared as described in Example 5, wherein polymer molecular weight is 28,000–40,000 and polymer concentrations vary between 5% to ~12% w/w. Compositions 5 and 6 are listed in Table 1.

Release profiles of the active core from the compositions in an aqueous physiological environment are described in Example 2 and are plotted as cumulative percentage release versus time, and presented in FIG. 5.

Burst-free, variable release from 28–70 days is achieved by varying the polymer concentration.

EXAMPLE 7

Microcapsule compositions are prepared as described in Example 6, wherein the aqueous/oil ratio varies between 1/5 to 1/25 (v/v). Compositions 3 and 7 are listed in Table 1.

Release profiles of the active core from the compositions in an aqueous physiological environment are described in Example 2, and plotted as cumulative percentage release versus time, and presented in FIG. 5.

Burst-free, variable release from 28–70 days is achieved by varying the aqueous/oil ratios.

EXAMPLE 8

Microcapsule compositions are prepared as described in Example 5, wherein the copolymer ratio is 75/25 and polymer concentrations vary between 5% to ~25% w/w. Compositions 8 and 9 are listed in Table 1.

Release profiles of the active core from the compositions in an aqueous physiological environment are described in Example 2, and are plotted as cumulative percentage release versus time, and presented in FIG. 3.

Burst-free, variable release from 56->90 days is achieved by varying the polymer concentration in the oil phase.

EXAMPLE 9

Figure 7:
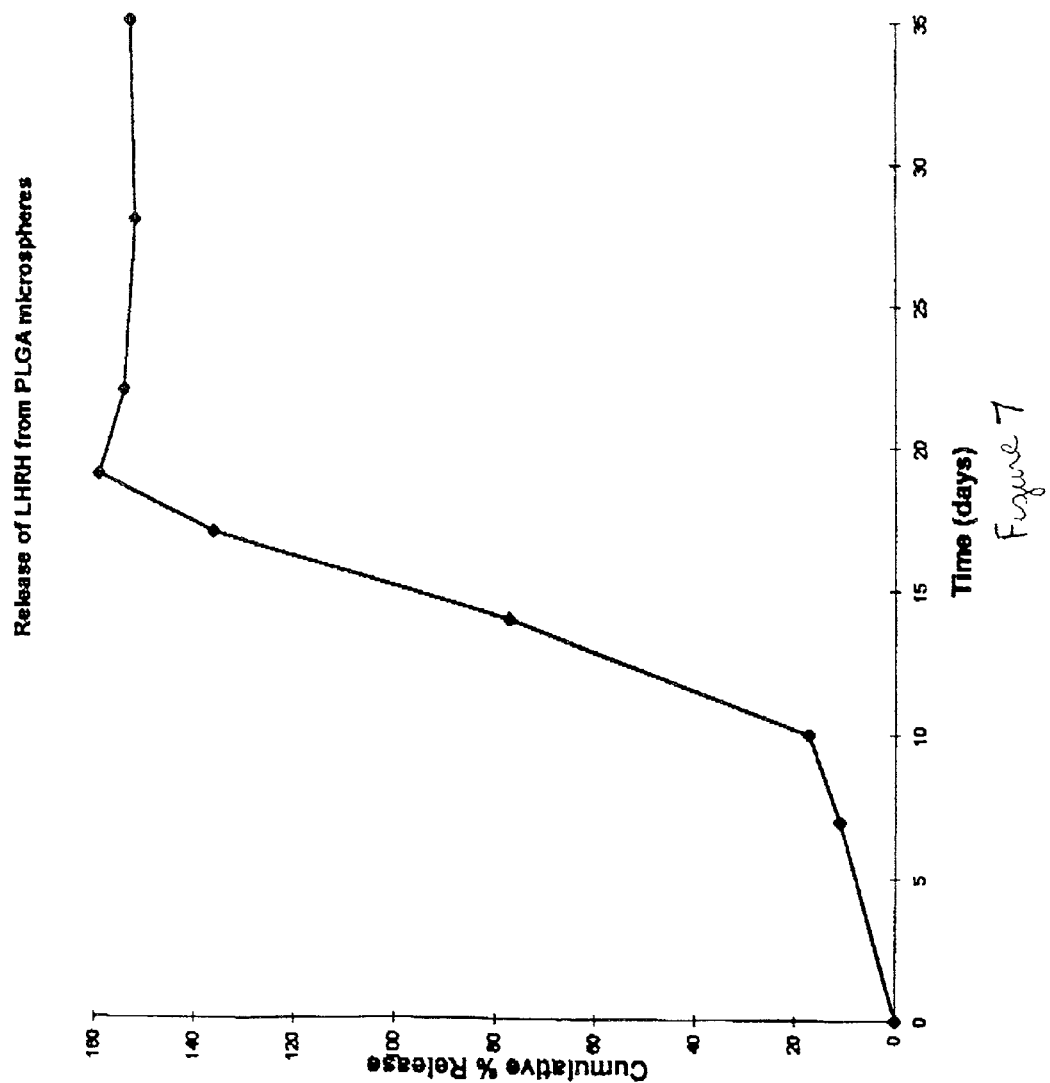
FIG. 7 shows a cumulative percent release of LHRH from PLGA microspheres prepared using uncapped polymer of Mw 8–12 daltons.

Microcapsule compositions are described in Example 2, wherein the active core is leutinizing hormone releasing hormone (LHRH, a decapeptide of molecular weight 1182) and the polymer concentration is ~40% w/w. Release profiles of the active core from the composition in an aqueous physiological environment are described in Example 2, They are plotted as cumulative percentage release versus time, and presented in FIG. 7.

Burst-free, continuous and complete release is achieved within 35 days, similar to Histatin acetate.

EXAMPLE 10

Microcapsule compositions are prepared as described in Example 2, wherein an additive such as sodium salt (carbonate or bicarbonate) is added to the inner aqueous phase at concentrations of 1–10% w/w to maintain the biological activity of the released polypeptide.

Burst-free, variable release from 1–28 days is achieved similar to Examples 2 & 3, and the released polypeptide is biologically active until 30 days, due to the presence of the sodium salt.

EXAMPLE 11

Microcapsule compositions are prepared as described in Example 2, wherein an additive such as a nonionic surfactant, polyoxyethylene/polyoxypropylene block copolymer (Pluronics F68 and F127) is added to either the inner oil or the aqueous phase at concentrations from 10–100% w/w, to maintain the biological activity of the released polypeptide.

Burst-free, continuous release from 1–35 days is achieved similar to Examples 2 & 3, and the released polypeptide is bioactive due to the presence of the surfactant.

EXAMPLE 12

Cumulative histatin release from the microcapsule compositions described in Examples 1 through 11 and release profiles plotted in FIGS. 3 and 5 show the burst-free, programmable peptide release for variable duration from 1–100 days. Virtually any pattern of cumulative release is achievable over a 100 day duration by a judicious blending of several compositions, as shown in FIG. 6.

We claim:

1. A process for preparing controlled release microcapsule formulations characterized by burst-free, sustained, programmable release of biologically active agents comprising: Dissolving biodegradable poly (lactide/glycolide), polymer in a form of uncapped/end-capped blend in a ratio of from 50/50 to 1/99 in methylene chloride, and dissolving a biologically active agent or active core in water; adding the aqueous layer to the polymer solution and emulsifying to provide an inner water-in-oil (w/o) emulsion; stabilizing said inner w/o emulsion in a solvent-saturated aqueous phase containing an oil-in-water (o/w) emulsifier; emulsifying said inner w/o emulsion in an external aqueous layer containing oil-in-water emulsifier to form a ternary emulsion; and stirring the resulting water-in-oil-in-water (w/o/w) emulsion for sufficient time to remove said solvent to harden microcapsules, and rinsing the hardened microcapsules with water and lyophilizing said hardened microcapsules.

2. The process of claim 1 wherein a solvent-saturated external aqueous phase is added to emulsify the inner w/o emulsion prior to addition of the external aqueous layer, to provide microcapsules of narrow size distribution range between 0.05–500 µm.

3. The process of claim 1 wherein a low temperature of about 0–4° C. is provided during preparation of the inner w/o emulsion, and a low temperature of about 4–20° C. is provided during preparation of the w/o/w emulsion to provide a stable emulsion and high encapsulation efficiency.

4. The process of claim 1 wherein a the blend of uncapped and end-capped polymer is used to provide release of the active core in a continous and sustained manner without a lag phase.

* * * * *